(12) United States Patent
Volger et al.

(10) Patent No.: US 9,528,155 B2
(45) Date of Patent: Dec. 27, 2016

(54) IN VITRO METHOD FOR DETERMINING IMMUNOTOXICITY OF A COMPOUND

(71) Applicants: UNIVERSITEIT MAASTRICHT, Maastricht (NL); ACADEMISCH ZIEKENHUIS MAASTRICHT, Maastricht (NL)

(72) Inventors: Oscar Leonard Volger, Amsterdam (NL); Jia Shao, Wageningen (NL); Adrianus Antonius Cornelis Maria Peijnenburg, Diemen (NL); Hendrik Van Loveren, Den Dolder (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 484 days.

(21) Appl. No.: 14/028,308

(22) Filed: Sep. 16, 2013

(65) Prior Publication Data

US 2014/0080734 A1    Mar. 20, 2014

(30) Foreign Application Priority Data

Sep. 14, 2012 (EP) .................................... 12184575

(51) Int. Cl.
 *C12Q 1/68* (2006.01)
 *G01N 33/50* (2006.01)

(52) U.S. Cl.
 CPC ........... *C12Q 1/6881* (2013.01); *G01N 33/505* (2013.01); *G01N 33/5014* (2013.01); *G01N 2333/705* (2013.01)

(58) Field of Classification Search
 None
 See application file for complete search history.

(56) References Cited

U.S. PATENT DOCUMENTS

2003/0040025 A1    2/2003    Ishihara et al.

OTHER PUBLICATIONS

Lankveld et al.; In Vitro Testing for Direct Immunotoxicity: State of the Art; Immunotoxicity Testing; vol. 598 of the series Methods in Molecular Biology; pp. 401-423; Oct. 30, 2009.*
Baken et al., Toxicogenomics in the Assessment of Immunotoxicity, ScienceDirect, 2007, pp. 132-141, vol. 41.
Gil et al., Biomarkers as Biological Indicators of Xenobiotic Exposure, Journal of Applied Toxicology, 2001, pp. 245-255, vol. 21.
Gupta et al., Toxicogenomics and Cancer Pathogenesis, International Journal of Genetics, 2009, pp. 47-60, vol. 1, No. 2.
Johansson et al., A Genomic Biomarker Signature Can Predict Skin Sensitizers Using a CellBased in Vitro Alternative to Animal Tests, BMC Genomics, 2011, pp. 1-19, vol. 12, No. 399.
Vos et al., Markers for Immunotoxic Effects in Rodents and Man, Toxicology Letters, 1995, pp. 385-394, vol. 82/83.
Partial European Search Report for EP 12184575.4 dated Dec. 5, 2012.
Extended European Search Report for EP 12184575.4 dated Apr. 2, 2013.

* cited by examiner

*Primary Examiner* — Antonio Galisteo Gonzalez
(74) *Attorney, Agent, or Firm* — TraskBritt, P.C.

(57) ABSTRACT

The invention is in the field of molecular diagnostics. More in particular it provides marker genes for determining the immunotoxicity of compounds. A method according to the invention employs samples obtained from a cell exposed to a potentially immunotoxic compound and determines expression levels of a number of marker genes in order to distinguish between immunotoxic compounds and non-immunotoxic compounds. More in particular, the invention relates to an in vitro method for determining whether a compound is immunotoxic wherein the expression level of at least one marker gene is determined in a sample obtained from a nucleated cell exposed to the compound, wherein the at least one marker gene is selected from the group consisting of ABCA1, CHAC1, CRIM1 and HMGCS1, and wherein it is concluded that the compound is immunotoxic if the expression level of said at least one marker gene is below or above a predetermined reference value.

15 Claims, No Drawings

IN VITRO METHOD FOR DETERMINING IMMUNOTOXICITY OF A COMPOUND

CROSS-REFERENCE TO RELATED APPLICATIONS

This application claims the benefit under the Paris Convention to EP 12184575.4 filed 14 Sep. 2012, the disclosure of which is hereby incorporated herein in its entirety by this reference.

FIELD OF THE INVENTION

The invention is in the field of molecular diagnostics. More in particular it provides marker genes for screening compounds for direct immunotoxicity. A method according to the invention employs samples obtained from a cell exposed to a compound of interest and determines expression levels of a number of marker genes in order to determine whether or not the compound is immunotoxic.

BACKGROUND OF THE INVENTION

During the registration processes of chemicals and drugs, within the European Union, United States of America, and Japan the current screening methods being applied for direct immunotoxicity are part of general toxicity testing. These toxicity tests are based on animal models, mainly consisting of rats, mice, and rabbits. The use of these animal models has three main drawbacks, mainly being ethical, economical, and the required translation towards the human situation can lead to false-positive and false-negative results. First, these tests cause suffering of the animals involved, which leads to societal concerns. Second, at present within the EU approximately 40 thousand chemicals are awaiting the process of registration, evaluation, and authorization (REACH). The EU has neither the infrastructure nor the economical means to test all of these chemicals in animal models. Third, the limited predictive power of these animal models for human toxicity complicates the processes of risk assessment of chemicals and safety testing of drugs. It has been shown in many instances that animal tests do not accurately predict immunotoxicity in humans.

False positive tests prevent many potentially useful drugs from reaching the market. False negatives cause human toxicity, either during the clinical-(I-III), and after-market phases (IV) of drug testing, or even later. At these stages, several millions of euros may already have been invested in vain. On average, the process of testing a chemical or drug for toxicity or safety takes years. This is partially caused by the time-consuming nature of animal tests.

Therefore, at the authorities and the industries involved in toxicity testing of chemicals and drug, there is a need for toxicity tests that are, ideally, more accurate, affordable, faster, and have less ethical concerns.

SUMMARY OF THE INVENTION

We now found that a reliable in vitro test may distinguish between immunotoxic and non-immunotoxic compounds. This method obviates the need for animal experiments and provides a 100% accurate result. Additional advantage is that the method can be performed within a few days.

Accordingly, the invention relates to an in vitro method for determining whether a compound is immunotoxic wherein the expression level of at least one marker gene is determined in a sample obtained from a nucleated cell exposed to the compound, wherein the at least one marker gene is selected from the group consisting of ABCA1, CHAC1, CRIM1 and HMGCS1, and wherein it is concluded that the compound is immunotoxic if the expression level of said at least one marker gene is below or above a predetermined reference value.

DETAILED DESCRIPTION OF THE INVENTION

We exposed a human cell line in an in vitro culture to a number of immunotoxic compounds (N=26, table 1) and control compounds (N=11, table 2). We then determined the expression levels of 4 marker genes (table 3) using a quantitative PCR assay.

Each of the marker genes on its own was able to predict the immunotoxicity of a compound with an acceptable level of accuracy (table 4). The invention therefore relates to an in vitro method for determining whether a compound is immunotoxic wherein the expression level of at least one marker gene is determined in a sample obtained from a nucleated cell exposed to the compound, wherein the at least one marker gene is selected from the group consisting of ABCA1, CHAC1, CRIM1 and HMGCS1, and wherein it is concluded that the compound is immunotoxic if the expression level of said at least one marker gene is below or above a predetermined reference value.

We also found that the reliability of the method improved when the expression level of more than one gene was determined. In a preferred embodiment, the invention therefore relates to a method as described above wherein the at least one marker gene is at least two marker genes, such as at least 3 marker genes such as at least 4 marker genes.

Surprisingly, we found that a 100% accurate prediction of immunotoxicity could be made based on only these 4 marker genes. 100% accuracy in this respect means that all immunotoxic compounds were predicted right and that none of the controls provided a positive result.

In a further preferred method, the invention therefore relates to a method as described above, wherein the expression level of all 4 marker genes is determined and wherein it is concluded that the compound is immunotoxic, if the expression level of at least one of the marker genes is below or above a predetermined reference value.

It should be noted that not all marker genes reacted in the same way on exposure of immunotoxic compounds. Some genes respond with upregulation, some with downregulation. Even within a single gene we observed downregulation upon exposure of one immunotoxic compound and upregulation upon exposure to anther compound (table 4).

The method according to the invention was found to be very robust. This robustness could even be improved when it is concluded that the compound is immunotoxic if the expression level of at least two of the marker genes is below or above a predetermined reference value. This compromises the sensitivity but may be advantageous when specificity is of importance.

The method could even be further improved when it is concluded that the compound is immunotoxic, if the expression level of at least three of the marker genes is below or above a predetermined reference value.

The expression levels of a marker gene are to be compared to a reference value, also often referred to as cut-off value. Such a reference value may be empirically determined or arbitrarily chosen in order to achieve appropriate specificity and/or sensitivity of the method. A skilled person is fully aware how to choose an appropriate reference value.

Such a reference value may advantageously be based on an expression value obtained with a control compound. A skilled person will know how to alter the predetermined reference value in order to obtain the desired specificity and sensitivity of the method.

The predetermined reference value may advantageously be a value obtained from the expression of a reference gene. Herein we used 3 genes as reference genes; beta-2-macroglobulin (B2M), Golgi to ER traffic protein 4 (GET4) and phosphatidylinositol glycan anchor biosynthesis class G1 (PIGG).

In the context of the present invention, the term "exposed" means "contacted" in the broadest sense of the word. Exposure means physically contacting the cell with the compound, such as, for instance, dissolving the compound in the culture medium of the cell. It is important that the cell is exposed to the compound at sub-cytotoxic levels and dosages.

The term "Gene Expression Ratio" or "Ratio," as used herein, refers to a number describing how much a quantity changes going from an initial to a final value. For example, an initial value of 30 and a final value of 60 correspond to a Ratio of 2, or in common terms, a two-fold increase. The Gene Expression Ratio is calculated simply as the ratio of the final value to the initial value, i.e., the control expression value. If the initial value is A and final value is B, the Ratio is B/A. As another example, a change from 80 to 20 would be a Ratio of 0.25, while a change from 20 to 80 would be a Ratio of 4. Herein, we replaced a Ratio that is less than 1 by the negative of its inverse, e.g., a change from 80 to 20 would be a fold change of −4 (or in common terms, a four-fold decrease). This is referred herein as "Fold Change." In the tables presented herein, we show the Fold Changes of overexpressed genes as values above 1.0 and underexpression as the negative inverse of the Ratio, i.e., values below −1.0.

Gene expression levels may be determined with every method known in the art for detecting nucleic acid expression levels. Methods, such as quantitative PCR, quantitative NASBA, gene sequencing such as next-generation sequencing, RNA sequencing, reporter gene assays or micro-array analysis are particularly preferred. Gene expression levels may also be determined by examining protein expressed by the marker genes, disclosed herein, for instance, by ELISA techniques.

When the threshold for positivity was chosen at 2.0 times, the reference value (or 0.5 times when downregulated, fold change is then −2) a 100% accuracy could be reached. Hence, the invention relates to a method, as described above, wherein it is concluded that the compound is immunotoxic, if the expression level of the marker genes is at least 2 times below or above a predetermined reference value.

The term "cell" in this context is to be interpreted as any cell, either isolated or in a tissue structure. It is preferred to use cells that may be cultured in vitro. Such is advantageous because the cell can then be contacted with the compound in the culture medium so as to ensure a uniform and reproducible contacting.

Advantageously, the cell is a human cell since that may reflect the immunotoxicity of the compounds towards humans best. We found that the cell may advantageously be a human lymphoblastic cell, preferably a Jurkat cell.

We found that the time of exposure is not critical, cells may be exposed to the compounds for several hours to several days, we choose an exposure time of 6 hours.

Methods, as described above, may be improved by using multiple individual samples, obtained from independently exposed cells. In that way, the expression level of a gene may be the average of a number of expression levels obtained for each individual gene.

TABLE 1

List of immunotoxic compounds.

| chemical name | Abbreviation | CAS number | Pubchem CID | exposure conc. (uM) |
|---|---|---|---|---|
| 1-Nitropyrene | 1-NPR | 5522-43-0 | 21694 | 50 |
| 6-mercaptopurine | 6MP | 6112-76-1 | 24888330 | 0.1 |
| arsenic trioxide | As2O3 | 1327-53-3 | 261004 | 3 |
| benzo[a]pyrene | BaP S9 | 50-32-8 | 2336 | 5 |
| cadmium dichloride | CdCl2 | 10108-64-2 | 24947 | 20 |
| cyclophosphamide | CP S9 | 6055-19-2 | 24278292 | 3000 |
| cyclosporine A | CsA | 59865-13-3 | 5280754 | 8 |
| dexamethasone | DEX | 50-02-2 | 5743 | 10 |
| deoxynivalenol | DON | 51481-10-8 | 40024 | 0.25 |
| O,O-Diethyl O-[4-methyl-6-(propan-2-yl)pyrimidin-2-yl] phosphorothioate (Diazinon) | DZN | 333-41-5 | 3017 | 200 |
| ethanol | EtOH | 64-17-5 | 702 | 343 |
| fingolimod | FTY720 | 162359-55-9 | 107969 | 4 |
| Gamma-hexachlorocyclohexane (Lindane) | LIN | 58-89-9 | 727 | 2000 |
| mono-(2-ethylhexyl) phthalate | MEHP | 4376-20-9 | 20393 | 300 |
| mycophenolic acid | MPA | 24280-93-1 | 446541 | 10 |
| methotrexate | MTX | 133073-73-1 | 4112 | 0.01 |
| nivalenol | NIV | 23282-20-4 | 430146 | 0.2 |
| ochratoxin A | OTA | 303-47-9 | 442530 | 8 |
| ochratoxin A, S9-treated | OTA S9 | 303-47-9 | 442530 | 10 |
| polychlorinated biphenyl 153 | PCB153 | 35065-27-1 | 37034 | 20 |
| PFOS | PFOS | 1763-23-1 | 74483 | 20 |
| 2-amino-1-methyl-6-phenylimidazo[4,5-b]pyridine | PhIP | 105650-23-5 | 1530 | 50 |
| prednisolone | PRD | 50-24-8 | 5755 | 500 |
| N-(3,4-Dichlorophenyl)propanamide (Propanil) | PROP | 709-98-8 | 4933 | 100 |
| tributyltin chloride | TBTC | 1461-22-9 | 15096 | 0.1 |
| tributyltin oxide | TBTO | 56-35-9 | 16682746 | 0.1 |

TABLE 2 list of control compounds.

| Controls | | | | |
|---|---|---|---|---|
| silver nitrate | AgNO3 | 7761-88-8 | 24470 | 1.35 |
| ampicillin | AMP | 69-53-4 | 6249 | 850 |
| azathioprine | AZA | 446-86-6 | 2265 | 0.1 |
| Bis(2-ethylhexyl)phthalate | DEHP | 117-81-7 | 8343 | 300 |
| trisodium citrate | NaCitrate | 8055-55-8 | 71474 | 2000 |
| dimethylnitrosamine | DMNA | 62-75-9 | 6124 | 34 |
| furosemide | FURO | 54-31-9 | 3440 | 100 |
| 2-amino-3-methyl-3H-imidazo[4,5-F]quinoline | IQ | 76180-96-6 | 53462 | 50 |
| MANNITOL | MANNITOL | 69-65-8 | 6251 | 2000 |
| N,N'-methylenebisacrylamide | MBA | 110-26-9 | 8041 | 200 |
| urethane | urethane | 51-79-6 | 5641 | 20000 |

TABLE 3

List of marker genes

| Gene symbol | Gene name | mRNA accession |
|---|---|---|
| HMGCS1 | 3-hydroxy-3-methylglutaryl-CoA synthase 1 (soluble) | NM_001098272 |
| CHAC1 | ChaC, cation transport regulator homolog 1 (E. coli) | NM_001142776 |
| CRIM1 | cysteine rich transmembrane BMP regulator 1 (chordin-like) | NM_016441 |
| ABCA1 | ATP-binding cassette, sub-family A (ABC1), member 1 | NM_005502 |

TABLE 4

Expression levels of marker genes upon exposure to immunotoxic compounds.

| | Genes | | | |
|---|---|---|---|---|
| | HMGCS1 | ABCA1 | CRIM1 | CHAC1 |
| Immunotox compounds | | | | |
| 1-NPR | −2.4 ± 1.1 | 1.3 ± 1.2 | 1.3 ± 1.6 | −1.2 ± 1.4 |
| PFOS | −1.1 ± 0.2 | −4.3 ± 0.2 | −1.5 ± 0.4 | 1.8 ± 1.5 |
| PRD | 1.7 ± 0.1 | 1.0 ± 0.6 | 3.9 ± 0.6 | 2.7 ± 1.9 |
| 6MP | −1.2 ± 0.0 | −3.2 ± 0.4 | 1.0 ± 0.6 | 1.8 ± 1.1 |
| CsA | 2.3 ± 0.5 | −1.8 ± 0.3 | 1.1 ± 0.7 | 3.1 ± 3.1 |
| DEX | 1.0 ± 0.1 | −2.0 ± 0.1 | 1.4 ± 0.6 | −1.2 ± 0.5 |
| DON | −1.5 ± 0.3 | −1.9 ± 0.2 | 1.4 ± 0.4 | −1.4 ± 0.4 |
| PCB153 | 2.0 ± 1.2 | 1.1 ± 1.4 | −1.2 ± 2.2 | 1.2 ± 3 |
| PhIP | −1.4 ± 1.1 | −2.2 ± 2.5 | −1.7 ± 2.5 | −1.1 ± 2.4 |
| MPA | −2.4 ± 0.0 | 1.1 ± 0.7 | −1.2 ± 0.1 | 1.5 ± 0.9 |
| MTX | −1.3 ± 0.2 | −1.8 ± 0.3 | 1.4 ± 1.1 | −1.1 ± 0.2 |
| NIV | 1.0 ± 1.2 | 1.1 ± 1.7 | 1 ± 1.9 | −1.5 ± 2.5 |
| PROP | −3.4 ± 0.1 | 1.3 ± 1 | 1.4 ± 0.1 | −1.1 ± 0.5 |
| BaP S9 | 1.1 ± 0.7 | 1.2 ± 1.5 | 1.0 ± 0.4 | −30.2 ± 0.0 |
| EtOH | −1.5 ± 1.1 | 1.2 ± 1.0 | −1.2 ± 1.2 | 34.3 ± 2.3 |
| FTY720 | 2.7 ± 0.5 | −2.8 ± 0.3 | −1.4 ± 0.3 | −1.6 ± 0.3 |
| MEHP | 1.6 ± 0.9 | −1.2 ± 0.1 | −1 ± 0.6 | 3.5 ± 2.1 |
| TBTC | −1.4 ± 0 | 40.8 ± 29.7 | 1.0 ± 0.1 | 1.3 ± 0.7 |
| TBTO | −1.5 ± 0.1 | 30.9 ± 8.5 | −1.1 ± 0.8 | −1.1 ± 0.4 |
| CP S9 | 2.0 ± 1 | 1.9 ± 1.6 | 1.1 ± 0.3 | −22.6 ± 0.0 |
| DZN | −1.9 ± 0.1 | 2.7 ± 2.8 | 4.0 ± 1.9 | 4.3 ± 3.8 |
| CdCl2 | 2.2 ± 1.3 | 1.3 ± 1.3 | 4.3 ± 2.0 | 7.0 ± 1.5 |
| OTA | −2.5 ± 0.1 | −2.2 ± 0.1 | −1.3 ± 0.1 | 32.9 ± 14.5 |
| As2O3 | −1.1 ± 0.2 | 1.4 ± 0.3 | 2.4 ± 1.1 | 41.2 ± 32.5 |
| OTA S9 | 2.0 ± 1.0 | 1.3 ± 1.8 | −1.1 ± 0.5 | −13.8 ± 0.0 |
| LIN | −2.4 ± 0 | 3.4 ± 3.6 | 2.3 ± 0.1 | 10.2 ± 7.6 |
| CONTROLS Non-immunotox | | | | |
| AgNO3 | 1.6 ± 0.9 | 1.5 ± 1.2 | 1.1 ± 0.3 | −1.1 ± 0.5 |
| AMP | 1.4 ± 0.3 | −1.7 ± 0.2 | 1.2 ± 1.1 | −1.5 ± 0.7 |
| AZA | 1.1 ± 0.2 | −1.9 ± 0.3 | 1.8 ± 1.0 | 2.3 ± 2.1 |
| DEHP | 1.2 ± 0.1 | −1.2 ± 0.3 | 1.9 ± 1.5 | −1.1 ± 0.4 |
| NaCitrate | −1.4 ± 0.4 | −2.0 ± 0.2 | 1 ± 0.2 | 1.1 ± 0.2 |
| DMNA | 1.2 ± 1.1 | −1.8± | −12 ± 1.5 | −1.5 ± 1.5 |
| FURO | 1.1 ± 0.2 | −1.4 ± 0.4 | 1.4 ± 0.5 | 1.6 ± 1.6 |
| IQ | −1.3 ± 1.1 | 1.0 ± 2.2 | 1.1 ± 1.8 | −1.1 ± 2.2 |
| MANNITOL | 1.2 ± 0.3 | −1.4 ± 0.3 | 1.1 ± 0.7 | −1.2 ± 0.2 |
| MBA | 1.0 ± 1.1 | −2.3 ± 2.1 | 1.1 ± 1.9 | 1.5 ± 2.1 |
| urethane | 1.2 ± 0.3 | −1.4 ± 0.1 | 1.1 ± 0.5 | 1.2 ± 0.4 |

EXAMPLES

Example 1

Cell Culture

The human lymphoblastic T-cell line (Jurkat) was obtained from the American Type Culture Collection (Jurkat clone E6-1, cat. No. TIB-152TM, ATCC). The Jurkat cells were grown in RPMI-1640 medium (Invitrogen) supplemented with 10% heat inactivated Fetal Calf Serum (FCS), 2 mM glutamine, 1 mM sodium pyruvate, 1 mM non-essential amino acid, 100 U/ml penicillin, and 100 μg/ml streptomycin. Cells were cultured at 37° C. with 5% CO2 in a humidified atmosphere. Jurkat cell cultures were maintained in T-75 flasks (GIBCO), at a volume of 30 mL, and medium was refreshed every 2 days.

Example 2

Compounds

We tested a number of known immunotoxic compounds in the method as described herein. Those compounds are listed in table A. As a control, eleven compounds were tested in the same method. These control compounds and their particulars are listed in table B. Stock solutions of all chemicals were made by dissolving the substances in dimethyl sulfoxide (DMSO; Merck, Darmstadt, Germany). Benzo[a]pyrene (BaP), ochratoxin A (OTA), and cyclophosphamide (CP) needed to be bio-activated before exerting their immunomodulatory effects (Carlson et al., Mar Environ Res. 2004 August-December; 58(2-5):731-4.; Ekhart et al. Cancer Treat Rev. 2009 February; 35(1):18-31, Manderville, Chem Res Toxicol. 2005 July; 18(7):1091-7). Therefore these compounds were subjected to an in vitro metabolic activation system using pooled S9 fractions of human livers containing hepatic enzymes. The S9 reaction mixtures, having a total volume of 1 ml, consisted of 570 μl H$_2$O (MQ), 200 μl 0.5 M potassium phosphate buffer (pH 7.4), 100 μl NADPH regeneration system solution A (BD Bioscience, Breda, the Netherlands), 20 μl NADPH regeneration system solution B (BD Bioscience, Breda, the Netherlands), 10 μl compound stock in DMSO, and 100 μl S9 mix (BD Bioscience, Breda, the Netherlands). After incubating for 1, 6, and 24 hours, respectively, the S9-chemical reaction mixtures were heat inactivated (5 minutes at 56° C.) and pooled at equal volumes.

Example 3

Selection Compound Exposure Concentrations

We determined dose-viability response curves for each compound, upon 24 h chemical exposures in a 96well plate format, in at least N=3 independent experiments. Two different assays were used as readout methods for viability, being the ATPLite assay, which determines the intracellular ATP content, and the WST-1 assay which determines mitochondrial dehydrogenase activity.

We also established the 24 h≤CV80 value for each compound. This means that for each compound we determined the highest concentration that gave a viability value of ≥80% upon exposing Jurkat cells for 24 hours. These values were separately determined for the ATPLite and WST-1 assays. These ≤CV80 values were used as final 6 h exposure concentrations for the mRNA expression profiling experiments that followed. If the ATPLite and WST-1 assays gave different CV80 values, the lowest value was chosen as final exposure concentration.

Example 4

WST-1 Assay

WST-1 (4-[3-(4-iodophenyl)-2-(4-nitrophenyl)-2H-5-tetrazolio]-1,3-benzene disulfonate, Roche Diagnostic Ned BV, Almere, the Netherlands) is a water soluble tetrazonium salt, which is cleaved by mitochondrial dehydrogenases to form a colored formazan complex and the amount of formazan correlates to the viability of the cells. Jurkat cells (11,000 per well) were plated 20 hours in advance in 96 well plates, thus at the starting point of exposure there were about 20,000 cells per well. Exposure was done in triplicate in 100 µl medium for 24 hours to increasing concentrations of compounds or to the vehicle controls. In the last 2 hours of exposure, 10 µl of WST-1 reagent was added. Absorbance was measured at 450 nm in a microplate reader (BioTek, Winooski Vt., USA).

Example 5

ATPlite Assay

ATPlite assay (Perkin Elmer, Oosterhout, the Netherlands) is based on the production of light caused by the reaction of ATP with added luciferase and D-luciferin. The emitted light is proportional to the amount of ATP, which is a marker for cell viability. Jurkat cells (11,000 per well) were plated 20 hours in advance in 96 well plates, thus at the starting point of exposure there were ~20,000 cells per well. Exposure was done in triplicate in 100 µl medium in 96 well plates for 24 hours to increasing concentrations of compounds or to the vehicle controls. After exposure, the assay was performed according the manufacturer's protocol.

Example 6

Chemical Exposures

Jurkat cells between passages 16 to 20 were used in the 6 hour exposure experiments. 750,000 cells were seeded in 2.7 ml medium per well in 6-well plates (GIBCO). After growing the cells for 20 hours, 0.3 mL of 10× concentrated compound stock solutions (37 degrees C. with 5% $CO_2$ in a humidified atmosphere), that had been pre-diluted 100× in Jurkat cell culture medium, were added to each well containing 2.7 mL of medium with the cells. During the exposures the final DMSO concentrations were kept at 0.1% for all the samples. The N=3 experiments were performed on different days by using Jurkat cells of different passages, respectively.

Example 7

Total RNA Isolations and cDNA Syntheses

After having been exposed to the compounds or vehicle controls for 6 hours, the cells were transferred to 15 mL vials (Greiner), followed by centrifugation (5 min at 300 g, 4° C.). Thereafter, medium was removed, and the pellets were resuspended in icecold PBS, followed by centrifugation (5 min at 300 g, 4° C.). Thereafter the cells were resuspended in RLT buffer containing 10% β-mercaptoethanol, snap-frozen in liquid Nitrogen (>5 minutes), and stored at −80° C. Total RNA was isolated by using the QIA shredder kit (Qiagen, cat. #79656), according to the manufacturer's protocol. Subsequent RNA purification was performed according to the manufacturer's protocol, by using the miRNeasy Mini kit (Qiagen, cat. #217004) including a DNase-1 treatment on column (Qiagen, cat. #79254). RNA yield was assessed spectrophotometrically (NanoDrop 2000, Thermoscientific, via Isogen-lifescience, De Meern, the Netherlands). Total RNA quality was determined by applying 250 nanogram of total RNA to automated gel electrophoresis using Experion chips (cat#700-7103, Experion, Biorad, Veenendaal, the Netherlands). Samples with RNA Quality Index (RQI) Numbers >8 were considered to be of sufficient quality. cDNA samples were synthesized from total RNA samples using miScript Reverse Transcription kit according to the manufacturer's protocol, using 250 nanogram of total RNA as sample input (cat# 218161, Qiagen, Venlo, Netherlands).

Example 8

Fluidigm Multiplex Real-Time Quantitative PCR experiments

The cDNA samples were subjected to 14 cycles of specific target amplification (STA), using a 0.2× mixture of all combined Taqman Gene Expression assays (primers/probe) and the Taqman PreAmp Master Mix (AppliedBiosystems), followed by 5-fold dilutions. Water was included as No Template Control (NTC).

The NTCs were also included in the STA reaction, to serve as a true negative control for the entire procedure. After the 5-fold dilution, the STA samples were mixed with the Taqman assays. Then each sample was dispensed onto the BioMark 96.96 Dynamic Array (Fluidigm, South San Francisco, Calif. 94080, USA, distributor Bioké, Leiden, The Netherlands). The empty assay positions were filled with No Assay Controls (NAC, in which the 20× assay mix was substituted with water.

The Biomark Dynamic Array was filled using the Biomark Integrated Fluidic Circuit Controller (Fluidigm, South San Francisco, Calif. 94080, USA). The filled BioMark 96.96 Dynamic Array was then placed into the Biomark Realtime PCR system (Fluidigm, South San Francisco, Calif. 94080, USA) where the thermal cycling reactions were performed and fluorescence was detected using a CCD camera. The default Taqman PCR protocol was used on the BioMark instrument with an annealing temperature of 60° C. and a total of 35 cycles of PCR. Pair-wise combinations of all samples were made with each of the assays in duplicate on the array.

Example 9

Analyses of Q-RT-PCR Data

At the end of each PCR cycle data was collected from the reaction chambers on each array, and Ct values were extracted using the BioMark Real-Time PCR analysis software version 3.0.2. The quality threshold was set at 0.65 (default value).

The relative mRNA expression levels were calculated for each individual sample by applying the delta-delta-CT method. Delta (1) was the correction for mRNA abundance by using reference genes, and Delta (2) was the correction for the vehicle controls (mostly DMSO). We used N=3 reference genes that had shown to be constantly expressed without being influenced by compound exposures (highest Pearson correlations with an mRNA expression ratio (compound/carrier control) of 1.0), in the microarray mRNA expression "compendium" dataset that consisted of N=256 samples. The three reference genes were beta-2-macroglobulin (B2M, high abundant), golgi to ER traffic protein 4 (GET4), and phosphatidylinositol glycan anchor biosynthesis class G1 (PIGG), respectively.

Example 10

Criteria Changed mRNA Levels Classifier Genes

Within the context of selecting classifier genes for immunotoxicity, a changed mRNA level is defined as follows:

Upon 6 hours of exposure to a sub-cytotoxic level of an immunotoxic compound the mRNA level of a classifier gene is either an increased, or decreased by ≥2.0-fold, as compared with 6 hour exposure to a vehicle control (such as 0.1% (v/v) DMSO, or medium), in at least two out of three independent exposure experiments.

A sub-cytotoxic level is defined in the section named Selection compound exposure concentrations. In short, a sub-cytotoxic level is defined as the highest concentration which has, upon 24 hours of exposure, a <20% effect on the viability of Jurkat cells, as determined by two separate assays (WST-1, Roche, and ATPLite, Perkin Elmer), and corrected for differences in cell density between test compound and vehicle control.

What is claimed is:

1. An in vitro method of detecting altered expression of at least one marker gene in response to a compound, the method comprising:
   exposing a nucleated cell to the compound;
   detecting the level of the at least one marker gene expressed by the nucleated cell after exposure to the compound; and
   detecting altered expression of the at least one marker gene if the level of expression of the at least one marker gene is above or below a predetermined reference value for the level of expression of the at least one marker gene;
   wherein the at least one marker gene is selected from the group consisting of ABCA1, CHAC1, CRIM1 and HMGCS1; and
   wherein the immunotoxicity of the compound is not known.

2. The method according to claim 1, wherein the expression levels of at least two marker genes selected from the group consisting of ABCA1, CHAC1, CRIM1 and HMGCS1 are determined.

3. The method according to claim 2, wherein the expression level of ABCA1, CHAC1, CRIM1 and HMGCS1 is determined.

4. The method according to claim 1, wherein altered expression of the at least one marker gene is detected if the expression level of the at least one marker gene is at least 2 times below or above the predetermined reference value.

5. The method according to claim 1, wherein the nucleated cell is cultured in vitro.

6. The method according to claim 5, wherein the nucleated cell is exposed to the compound in the in vitro culture.

7. The method according to claim 1, wherein the nucleated cell is a human cell.

8. The method according to claim 7, wherein the nucleated cell is a Jurkat cell.

9. The method according to claim 1, wherein the nucleated cell is exposed to the compound for a time period ranging from several hours to several days.

10. The method according to claim 1, wherein the predetermined reference value is a value obtained from the expression of a reference gene.

11. The method according to claim 10, wherein the reference gene is selected from the group consisting of beta-2-macroglobulin, Golgi to ER traffic protein 4 and phosphatidylinositol glycan anchor biosynthesis class G1 isoform 1, or isoform 2.

12. The method according to claim 1, wherein detecting the level of the at least one marker gene expressed by the nucleated cell after exposure to the compound comprises obtaining multiple individual samples from independently exposed cells and wherein the expression level is the average of the individual expression levels of each individual gene.

13. The method according to claim 1, wherein the at least one marker gene is at least three marker genes.

14. The method according to claim 1, wherein the at least one marker gene is at least four marker genes.

15. The method according to claim 7, wherein the human cell is a human lymphoblastic cell.

* * * * *

UNITED STATES PATENT AND TRADEMARK OFFICE
CERTIFICATE OF CORRECTION

PATENT NO.          : 9,528,155 B2
APPLICATION NO.     : 14/028308
DATED               : December 27, 2016
INVENTOR(S)         : Volger et al.

Page 1 of 1

It is certified that error appears in the above-identified patent and that said Letters Patent is hereby corrected as shown below:

In the Specification

Column 1, Line 46, change "clinical-(I-III), and" to --clinical- (I-III), and--

Signed and Sealed this
Twenty-fourth Day of July, 2018

Andrei Iancu
*Director of the United States Patent and Trademark Office*